(12) United States Patent
Mann et al.

(10) Patent No.: US 9,226,992 B2
(45) Date of Patent: Jan. 5, 2016

(54) IMPLANTABLE CARTILAGINOUS TISSUE REPAIR DEVICE

(75) Inventors: Stephen Mann, Bristol (GB); David Philip Knight, Newbury (GB); Nicholas James Vavasour Skaer, Newbury (GB); Caroline Bertram, Hampshire (GB); Richard O. C. Oreffo, Romsey (GB); Helmtrud I. Roach, Romsey (GB); Andrew Michael Collins, Somerset (GB)

(73) Assignee: Orthox Limited, Oxfordshire (GB)

( * ) Notice: Subject to any disclaimer, the term of this patent is extended or adjusted under 35 U.S.C. 154(b) by 590 days.

(21) Appl. No.: 12/063,966

(22) PCT Filed: Aug. 17, 2006

(86) PCT No.: PCT/GB2006/003079
§ 371 (c)(1),
(2), (4) Date: Dec. 22, 2008

(87) PCT Pub. No.: WO2007/020449
PCT Pub. Date: Feb. 22, 2007

(65) Prior Publication Data
US 2009/0171467 A1    Jul. 2, 2009

(30) Foreign Application Priority Data
Aug. 17, 2005 (GB) .................. 0516846.3

(51) Int. Cl.
*A61F 2/28* (2006.01)
*A61L 27/42* (2006.01)
(Continued)

(52) U.S. Cl.
CPC ........... *A61L 27/227* (2013.01); *A61F 2/30756* (2013.01); *A61F 2/442* (2013.01);
(Continued)

(58) Field of Classification Search
CPC ....... A61L 27/227; A61L 27/48; A61L 27/52; A61L 27/56; A61F 2/30756; A61F 2/442
USPC .......... 623/14.12, 23.55, 23.57–23.61, 16.11, 623/17.11, 17.17, 18.11, 23.51, 23.63; 424/424, 426
See application file for complete search history.

(56) References Cited

U.S. PATENT DOCUMENTS

| 5,007,934 A | 4/1991 | Stone |
| 6,027,744 A | 2/2000 | Vacanti et al. |

(Continued)

FOREIGN PATENT DOCUMENTS

| EP | 0 372 811 | 6/1990 |
| EP | 1 493 404 | 1/2005 |

(Continued)

OTHER PUBLICATIONS

Altman G H et al.; "Silk-based biomaterials," Biomaterials, Elsevier Science Publishers BV; Feb. 2003.

(Continued)

*Primary Examiner* — Marcia Watkins
(74) *Attorney, Agent, or Firm* — Renner, Otto, Boisselle & Sklar, LLP

(57) ABSTRACT

A cartilaginous tissue repair device with a biocompatible, bioresorbable three-dimensional silk or other fiber lay and a biocompatible, bioresorbable substantially porous silk-based or other hydrogel partially or substantially filling the interstices of the fiber lay; with or without an integral means of firmly anchoring the device to a patient's bone.

20 Claims, 5 Drawing Sheets

(51) Int. Cl.

| | | |
|---|---|---|
| *A61L 27/52* | (2006.01) | |
| *A61L 27/56* | (2006.01) | |
| *A61L 27/58* | (2006.01) | |
| *A61F 2/38* | (2006.01) | |
| *A61F 2/44* | (2006.01) | |
| *A61L 27/22* | (2006.01) | |
| *A61F 2/30* | (2006.01) | |
| *A61L 27/48* | (2006.01) | |

(52) U.S. Cl.
CPC ............... *A61L 27/48* (2013.01); *A61L 27/52* (2013.01); *A61L 27/56* (2013.01); *A61F 2/3872* (2013.01); *A61F 2002/30062* (2013.01); *A61F 2002/30075* (2013.01); *A61F 2002/3092* (2013.01); *A61F 2002/30766* (2013.01); *A61F 2002/4495* (2013.01); *A61F 2210/0004* (2013.01); *A61F 2210/0061* (2013.01)

(56) References Cited

U.S. PATENT DOCUMENTS

| | | | |
|---|---|---|---|
| 6,306,169 | B1 | 10/2001 | Lee et al. |
| 6,946,003 | B1 | 9/2005 | Wolowacz et al. |
| 2003/0083389 | A1* | 5/2003 | Kao et al. .................. 516/98 |
| 2003/0095994 | A1 | 5/2003 | Geistlich et al. |
| 2004/0197373 | A1* | 10/2004 | Gertzman et al. ............ 424/423 |
| 2004/0224406 | A1* | 11/2004 | Altman et al. ................ 435/395 |
| 2004/0241145 | A1 | 12/2004 | Hata et al. |
| 2004/0266992 | A1* | 12/2004 | Migliaresi et al. ............ 530/353 |
| 2007/0041952 | A1* | 2/2007 | Guilak et al. ................ 424/93.7 |
| 2007/0187862 | A1* | 8/2007 | Kaplan et al. ............ 264/172.11 |

FOREIGN PATENT DOCUMENTS

| | | | |
|---|---|---|---|
| JP | H01-308431 A | 12/1989 | |
| JP | H04-504968 A | 9/1992 | |
| JP | 2001-254264 A | 9/2001 | |
| JP | 2002-512842 A | 5/2002 | |
| JP | 2003-500162 A | 1/2003 | |
| JP | 2003-180815 A | 7/2003 | |
| JP | 2003-265169 A | 9/2003 | |
| WO | 89/00413 | 1/1989 | |
| WO | 90/09769 | 9/1990 | |
| WO | 91/16867 | 11/1991 | |
| WO | WO 96/35780 | * 11/1996 | ............ C12N 11/14 |
| WO | 00/72782 | 12/2000 | |
| WO | 03/018077 A1 | 3/2003 | |
| WO | 03/022909 | 3/2003 | |
| WO | 03/088925 | 10/2003 | |
| WO | 2005/000483 | 1/2005 | |
| WO | 2005/012606 | 2/2005 | |

OTHER PUBLICATIONS

International Search Report mailed Apr. 4, 2007.
International Preliminary Report on Patentability issued Feb. 20, 2008.
Tabata Yasuhiko, "Present Status of Regenerative Medical Therapy and Its Potential in Dentistry", J Jpn Prosthodont Soc 49, 2005, pp. 563-568 with English translation of Abstract.
Tsukada et al., "Chemical Modification of *Tussah Silk* with Acid Anhydrides", Journal of Applied Polymer Science, vol. 78, 2000, pp. 382-391.
Chen et al., "Biodegradable hybrid scaffolds for tissue engineering", Mar. 15, 2001 pp. 70-71, with English translation of Abstract.

* cited by examiner

IMPLANTABLE CARTILAGINOUS TISSUE REPAIR DEVICE

This application is a national phase of International Application No. PCT/GB2006/03079 filed Aug. 17, 2006 and published in the English language.

FIELD OF THE INVENTION

The present invention relates generally to surgical devices for approximating, repairing or regenerating damaged or diseased cartilage, and to manufacturing methods for such devices. In particular, the present invention relates to a device for the replacement, partial replacement or augmentation of damaged cartilage applicable to the repair of articular cartilage, the meniscus of the knee, the tempero-mandibular joint or an intervertebral disc.

BACKGROUND OF THE INVENTION

Cartilage in the adult mammalian body occurs in three principal forms: hyaline cartilage; white fibrocartilage; and yellow elastic cartilage. Hyaline cartilage is chiefly present as articular cartilage in the synovial diarthroidal joints of the hip and shoulder and between the long bones where it forms the stiff and smooth articulating surfaces. White fibrocartilage is present in the menisci of the knee and temporomandibular joint of the jaw and in the intervertebral discs. Yellow elastic cartilage gives support to the epiglottis, Eustachian tube and external ear.

Three pathological conditions involving cartilage damage are very common: osteoarthrosis of articular cartilage; injury to the fibrocartilage of the knee menisci and collapse, rupture or herniation of the intervertebral disc.

Osteoarthrosis is caused by the progressive damage and breakdown of articular cartilage most commonly in the hip and knee and is an important cause of pain and reduced mobility in old people. Injury to the fibrocartilage of the meniscus is a common sports injury and is also seen as a result of road traffic accidents.

The structure and function of articular cartilage has been reviewed by Hasler E M, Herzog W, Wu J Z, Muller W, Wyss U. 1999 in their article, "Articular cartilage biomechanics: Theoretical models, material properties, and biosynthetic response" published in Critical Reviews In Biomedical Engineering vol 27 part 6 pages 415-488. Articular cartilage is highly specialized to provide a relatively frictionless, highly lubricated, wear resistant surface between relatively rigid bones. It also functions to transmit and distribute the forces arising from loaded contact to the surrounding cartilage and underlying subchondral trabecular bone. Hyaline cartilage is not thought to act as a shock absorber limiting the forces to the bone from impacts. This is because its volume for dissipating energy is very small compared to that of bone and because it actually increases in stiffness with increasing strain rate making it an inappropriate material for use as a shock absorber. Articular cartilage is a non-vascular connective tissue largely composed of a fluid phase consisting principally of water and electrolytes interspersed in a solid phase containing type II collagen, proteo-glycan and other glycoproteins. The latter constituents surround and are secreted by highly specialized mesenchymal cells, the chondrocytes which account for some 10% of the volume of articular cartilage. Healthy articular cartilage is strong and stiff (modulus between 1 and 20 MPa). The arrangement of the collagen fibrils within articular is essential to its function. They are arranged in a complex arcade structure forming columns arranged normal to and anchored in the osteochondral junction. These columns run up through the deep layer of cartilage but the predominant fibre orientation gradually changes to form the arches of the arcade structure in the superficial cartilage.

In the superficial layer which abuts the joint space, the meshwork of collagen fibrils is much denser while the fibrils are almost entirely tangential to the cartilage surface. The orientation of collagen in articular cartilage is vital to its mechanical function.

No wholly satisfactory procedure exists for replacing damaged articular cartilage in osteoarthrosis and instead artificial prostheses are most commonly used to replace the entire hip and knee joints. While these increase mobility and reduce pain they suffer from progressive wear, mechanical failure, adverse tissue reactions and loosening at their interphase with the bone.

The menisci of the knee joint are C-shaped discs interposed between the femoral condyles and tibial plateau and have the function of compressive load spreading, shock absorption, stabilization and secretion of synovial fluid for lubrication. The structure, function and pathology of the menisci have been reviewed by S. M. Bahgia and M. Weinick, Y. Xing, and K. Gupta (2005) Meniscal Injury, E-medicine World Library, 27 Jul. 2005. The outer rim is vascular while the central part is avascular fibrocartilage. Type I collagen (non-articular cartilage fibrillar collagen) accounts for about 70% to 90% of the collagen of the menisci. Most of the collagen is arranged in rope-like circumferential fibres together with fewer radial tie fibers. As in articular cartilage, collagen orientation is extremely important for the mechanical function and fixation of this structure. Compression of the meniscus leads to tensile hoop loading of the circumferential fibres and radial loading of the radial fibres, resisting spreading and flexing of the menisici. Thus the ability of the meniscus to spread load and dissipate energy is dependent on the integrity of the collagen fibre lay. For this reason damage to these fibres increases the risk of secondary osteoarthrotic damage to the condylar cartilages as the normal load distribution and shock-absorbing functions are impaired. The meniscofemoral ligament firmly attaches the posterior horn of the lateral meniscus to the femoral condyle and the coronary ligament anchors the peripheral meniscal rim to the tibia.

Meniscal injuries are fairly common in adults and are most frequently sports-related. They are less common in children over 10 years old and rare in children under 10 with morphologically normal menisci (Iobst, C. A. and Stanitski, C. L., 2000, Acute knee injuries. Clin Sports Med. 2000 Oct.; 19 (4):621-35).

Surgical treatment of damaged menisci is often necessary. Although total or partial meniscectomy was popular some forty years ago, it is now well understood that this procedure leads to articular cartilage degeneration (King, D. Clin. Orthop. 1990, 252, 4-7; Fairbank, T. J. J. Bone Joint Surg. Br. 1948, 30, 664-670). The extent of the degeneration of the cartilage appears to depend on how much tissue has been removed. Therefore partial meniscectomy is the current procedure of choice. However, even with partial mensicectomy, secondary osteoarthrosis is still a long-term consequence. Better alternatives to partial meniscectomy are therefore being sought. Allograft transplantation is a fairly successful alternative. However there is no proof that replacement of the meniscus with an allograft can re-establish some of the important meniscal functions, and thereby prevent or reduce the development of osteoarthrosis secondary to meniscectomy (Messner, K. and Gao, J. 1998 The menisci of the knee joint. Anatomical and functional characteristics, and a rationale for clinical treatment. Journal of Anatomy, 193:161-

178). The major problems are the lack of remodelling of the graft resulting in inferior structural, biochemical and mechanical properties and insufficient fixation to bone. Further disadvantages include the shortage of suitable donors, difficulties with preservation techniques, the possible transfer of diseases, difficulty in shaping the implant to fit the donor and possible immunological reactions to the implant (Stone, K. R. Clin. Sports Med. 1996, 15, 557-571).

Total knee replacement cannot be considered as treatment for uncomplicated meniscal injury. Dacron and Teflon meniscal prosthetic components may initiate severe synovial reactions (Cook, J. L., Tomlinson, J. L., Kreeger, J. M., and Cook, C. R. 1999. The American Journal of Sports Medicine 27:658-665 Induction of meniscal regeneration in dogs using a novel biomaterial) while loosening and mechanical failure are a problem (de Groot, J. H. 1995 Doctoral dissertation. University of Gronigen, Summary p 153).

Partial or total meniscal replacements made from collagen, Teflon fibre, carbon fibre, reinforced polyester, or polyurethane-coated Dacron showed high failure rates resulting from poor fixation, mechanical failure or severe inflammatory response.

Elastomers based on amphiphilic urethane block copolymers have been suggested for meniscal repair and tested in an animal model. (Heijkants, R. G. J. C. 2004 Polyurethane scaffolds as meniscus reconstruction materials, Ph.D. Thesis, University of Groningen, The Netherlands, MSC Ph.D.-thesis series 2004-09; ISSN: 1570-1530; ISBN: 90 367 2169 5, chapter 10 pp 167-184) These materials are likely to produce less toxic degradation products than Dacron or Teflon. However, the mechanical properties of the polyurethanes tested did not match native meniscus very well and this may help to explain why only poorly orientated collagen was found in the regenerating fibro-cartilage in the implanted devices in place of the well-orientated collagen in normal meniscus. A further potential problem was that the polyurethane materials produced a Stage I inflammatory response (giant cells and some macrophages).

Recently, tissue engineering strategies for meniscal repair have been suggested including the use of biocompatible grafts as a substrate for regeneration, and cellular supplementation to promote remodeling and healing. Little is known, however, about the contributions of these novel repair strategies to restoration of normal meniscal function. (Setton, L. A., Guilak, F, Hsu, E. W. Vail, T. P. (1999) Biomechanical Factors in Tissue Engineered Meniscal Repair. Clinical Orthopaedics & Related Research. (367S) supplement:S254-S272, October 1999).

U.S. Pat. No. 4,344,193 (Kenny/Dow Chemical) appears to have been the first patent document to disclose the idea of a meniscal prosthesis rather than a total joint replacement endoprostheses. The meniscal prosthesis suggested is of non-reinforced silicone rubber. This material has low biocompatibility and would be likely to trigger a severe synovial reaction.

U.S. Pat. No. 4,502,161 (Wall) discloses a meniscal prosthesis of silicone rubber, rubber or polytetrafluorethylene with a reinforcing mesh of stainless steel strands, nylon or a woven fabric embedded within it. The suggested materials have low biocompatibility and would be likely to trigger a severe synovial reaction.

WO 89/00413 (Stone/Regen Biologics Inc.) discloses a prosthetic meniscus made of a three-dimensional array of collagen type I fibres interconnected via crosslinks consisting of polymerised glycosaminoglycan molecules. In vivo, the matrix has an outer surface contour substantially the same as that of a natural meniscus. The matrix provides a partially resorbable scaffold adapted for the ingrowth of meniscal fibrochondrocytes. Whilst the constructs may have a defined shape and size, the mechanical properties—in particular the compressive modulus—do not approach that of cartilage.

U.S. Pat. No. 4,919,667 (Richmond/Stryker) discloses a meniscal prosthesis constructed from polyester bonded with polyurethane. The polyester is arranged as a felt in one or more intermediate layers sandwiched between a woven cloth top and bottom layer also of polyester. The polyester and polyurethane are likely to be more biocompatible than the materials of U.S. Pat. No. 4,502,161.

U.S. Pat. No. 6,306,169 (Lee) discloses an implant consisting of a porous macrostructure the pores of which are filled up with a hydrated gel. The macrostructure is made of a bioresorbable polymer (collagen, gelatin, poly-L-lactic acid, polycaprolactone, polyhydroxybutarate, or polyanhydrides) and the non-porous, hydrated gel consists of alginate, agarose, carrageenans, glycosaminoglycans, proteoglycans, polyethyelene oxide or collagen monomers. This structure improves on the mechanical properties of the constructs of WO 89/00413, but still struggles to reach those of cartilage.

U.S. Pat. Nos. 6,514,515 and 6,867,247 (Williams) discloses the use of a bioresorbable and biocompatible polymer of polyhydroxyalkanoate for tissue repair. Such polymers may be tuned to have specific mechanical properties.

U.S. Pat. No. 6,679,914 (Gabbay) discloses a meniscal prosthesis comprising a plurality of superimposed sheets of animal pericardium cross-linked by an aldehyde.

WO 00/72782 (Wolowacz/Smith & Nephew) discloses a biocompatible, resorbable implantable material for total replacement or reinforcement of connective tissue consisting of a flexible tape containing aligned fibres. The application mentions the use of a hydrogel as a 'carrier medium' by means of which cells are incorporated into the material.

The structure and function of the intervertebral disc has been reviewed by Matcher, S J, Winlove, C P and Gangnus, S V., (2004) in their article, "The collagen structure of bovine intervertebral disc studied using polarization-sensitive optical coherence tomography" published in Physics in Medicine and Biology, volume 49 pages 1295-1306. A disc comprises an inner region, the nucleus pulposus surrounded by the annulus fibrosus. The inner nucleus pulposus is a visco-elastic gel constructed from proteoglycans trapped in a disordered network of fine type-II collagen fibrils. In contrast, the outer annulus fibrosus consists of axially concentric lamellae, constructed from larger fibrils of type I collagen and a considerably lower concentration of proteoglycans. The fibres run parallel to each other within each lamella of the annulus fibrosus but at a constant angle to the axis of the disc. This angle alternates from lamella to lamella to give a trellis-like structure in which the fibre angle increases as the disc is axially compressed. Thus the intervertebral disc has a somewhat similar structure and function to the meniscus, acting as a fluid-filled pressure vessel, whose function is to convert axial compressive forces into tensile forces in the collagen of the concentric lamellae of the annulus fibrosus. The collagen fibres of the annulus fibrosus at top and bottom of the disc are firmly anchored to the epiphyseal bone of the centra of the adjacent vertebrae.

WO 2005/094911 (Knight/Oxford BioMaterials Ltd.) discloses a composite material comprising one or more silk elements in an acrylic or cross-linked protein matrix and its use in a wide range of implantable devices. The application teaches the use of certain Wild silks naturally decorated with the integrin-binding tripeptide RGD. This tripeptide in Wild silks facilitates the binding of mesenchymal and other cells.

Thus, there is still considerable scope for improvement in the implantable materials and devices used for the repair or replacement of articular cartilage, intervertebral discs and menisci.

It is an object of the present invention to provide an implantable cartilaginous tissue repair device with mechanical properties which are closer to the anatomical requirements of the tissue to be repaired than those of prior art devices.

It is a further object of the present invention to provide a substantially bioresorbable implantable cartilaginous tissue repair device which allows and encourages the gradual infiltration and replacement of at least some parts of the device with autologous collagen and proteoglycans (i.e. collagen and proteoglycans produced by the patient's own body) more effectively than prior art devices.

In another aspect, it is an object of the present invention to provide an implantable tissue repair device which is at least partially bioresorbable and which has an effective means for being attached or anchored to a bone of a patient.

SUMMARY OF THE INVENTION

The invention provides an implantable cartilaginous tissue repair device comprising a biocompatible and at least partially bioresorbable three-dimensional fibre lay at least partially infiltrated by a biocompatible and at least partially bioresorbable, substantially porous hydrogel, whereby, in use, cells are contained within the pores of the device.

In another aspect the invention provides a method for the manufacture of an implantable cartilaginous tissue repair device comprising the steps of forming a three-dimensional fibre lay from biocompatible and at least partially bioresorbable fibres by one or more of the methods of: winding or weaving or compressing felts or twisting or knitting or braiding or stitching or embroidery or combining layers of cloth, preparing a biocompatible and at least partially bioresorbable, substantially porous hydrogel and either during or after production of said three-dimensional fibre lay, infiltrating said three-dimensional fibre lay with said biocompatible and at least partially bioresorbable, substantially porous hydrogel.

In another aspect the invention provides a method for the manufacture of an implantable tissue repair device comprising the steps of (I) forming a three-dimensional fibre lay from biocompatible and at least partially bioresorbable fibres by one or more of the methods of winding or weaving or compressing felts or twisting or knitting or braiding or stitching or embroidery (II) preparing a biocompatible and at least partially bioresorbable hydrogel (III) either during or after production of said three-dimensional fibre lay, infiltrating said three-dimensional fibre lay with said biocompatible and at least partially bioresorbable hydrogel (IV) mineralising at least one surface of said implantable tissue repair device by (IVa) preparing a buffered phosphate solution (IVb) adding said buffered phosphate solution to the hydrogel contained within said surface of said implantable tissue repair device (IVc) controlled freezing and/or drying of said surface of said implantable tissue repair device (IVd) exposing said surface of said implantable tissue repair device to a buffered calcium chloride solution.

In another aspect the invention provides an implantable tissue repair device comprising a biocompatible and at least partially bioresorbable fibre lay at least partially infiltrated by a biocompatible and at least partially bioresorbable hydrogel and an integral attachment means for attaching said fibre lay and/or said hydrogel to bone comprising at least one mineralised surface.

In another aspect the invention provides an implantable tissue repair device comprising a biocompatible and at least partially bioresorbable, mineralised hydrogel.

In another aspect the invention provides a method for the manufacture of an implantable tissue repair device comprising the steps of (I) preparing a biocompatible and at least partially bioresorbable hydrogel (II) mineralising said hydrogel by (IIa) preparing a buffered phosphate solution (IIb) adding said buffered phosphate solution to the hydrogel (IIc) controlled freezing and/or drying of said hydrogel (IId) exposing said hydrogel to a buffered calcium chloride solution.

The present invention provides an implantable cartilaginous tissue repair device with mechanical properties which are closer to the anatomical requirements of the tissue to be repaired than those of prior art devices. Indeed, an appropriately constructed device according to the present invention is capable of carrying out the mechanical functions of replaced tissue from the moment of implantation.

The present invention also provides a substantially bioresorbable implantable cartilaginous tissue repair device which allows and encourages the gradual infiltration and replacement of at least some parts of the device with autologous collagen and proteoglycans (i.e. collagen and proteoglycans produced by the patient's own body) more effectively than prior art devices. The porosity of the hydrogel allows, in particular, for infiltration by mesenchyme or stem cells.

The present invention provides a device of composite construction which enables the mechanical properties of the prosthesis to be tuned locally to provide appropriate stress/strain environments throughout the prosthesis to avoid the problem of stress shielding thereby encouraging the de novo formation of the correct connective tissues appropriate to the different locations of a complex tissue.

The three-dimensional fibre lay and constrained porous hydrogel impart cartilage-like properties to the implantable device enabling it to distribute stresses during compressive loading and, in the case of menisci and intervertebral discs, to act as a shock absorber.

In some embodiments, the orientation of collagen fibres in the natural tissues is mimicked in the implantable device of the present invention, giving it anisotropic mechanical properties similar to those of the natural tissue.

In some embodiments of the invention, the present invention provides an implantable tissue repair device which is at least partially bioresorbable and which has an effective means for being attached or anchored to a bone of a patient.

In some embodiments, an integral means of attaching or anchoring the implantable device firmly to the bone of a patient helps to overcome a persistent weakness of many orthopaedic devices—mechanical failure at the bone/prosthesis interface. The mineralisation of such an integral means of firmly attaching or anchoring the device, as used in some embodiments of the invention, provides a tough, compression-resistant material which would also facilitate fixation with a polylactic acid screw ('poly screw') or equivalent device in a drilled tunnel in the bone, thereby providing a strong and tough attachment to the bone.

In some embodiments of the invention, a high density three-dimensional fibre lay of strong, elastic and tough silk fibres entraps a porous hydrogel matrix cross-linked to the silk fibres, which gives a tough, resilient composite material with a high modulus.

In some embodiments of the invention, the resorption rates of silk fibres in the three-dimensional fibre lay and/or of silk protein hydrogel can be regionally tuned by controlled covalent cross-linking, controlled formation of β-sheet crystallinty and/or by tuning the hydrophobicity of the protein by alkylating with hydrophobic side chains. This enables the planning of an orderly 'hand over' of stress to the newly forming connective tissues during resorption without stress shielding.

In some embodiments, regionally specific growth factors are incorporated into some or all of the implantable device which encourage appropriate cell recruitment, differentiation and secretion which thus further facilitates the conversion over time of the device to regionally appropriate connective tissue.

Further objectives and advantages of the invention will become apparent from a consideration of the ensuing description and drawings, which, by way of example, describe embodiments of the invention providing implantable cartilaginous tissue repair devices for repairing or replacing knee meniscus (a 'meniscal repair device'), intervertebral discs (an 'intervertebral disc repair device') and articular cartilage (an 'articular cartilage repair device'). The exemplary embodiments consist of three-dimensional fibre lays of wild silk fibres infiltrated by a porous regenerated silk fibroin hydrogel.

DETAILED DESCRIPTION OF THE INVENTION

Figure 1:
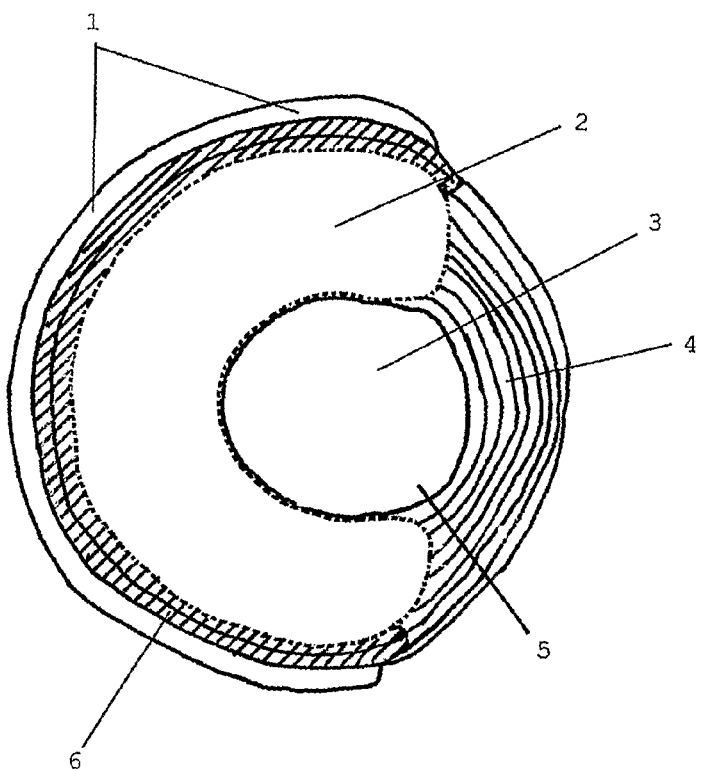
FIG. 1: A schematic plan drawing of a meniscal repair device according to the invention.
Figure 2:
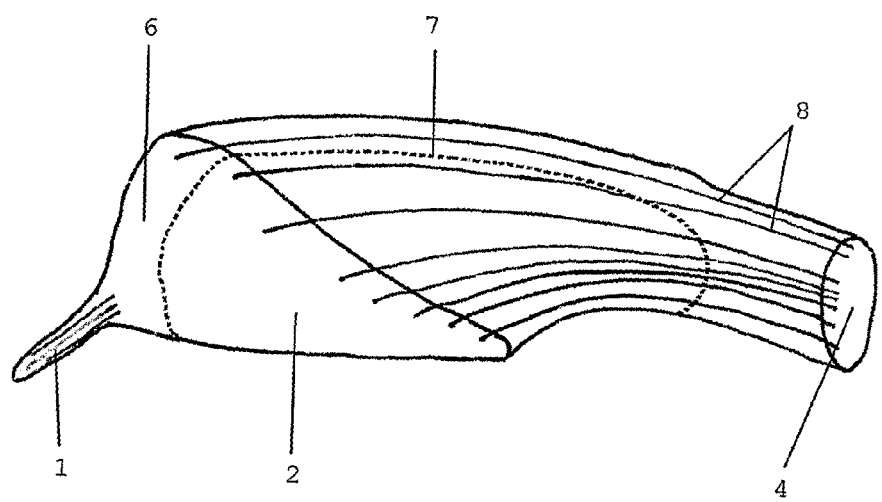
FIG. 2: A schematic cross-sectional perspective drawing of a meniscal repair device according to the invention.

FIGS. 1 and 2 are respectively a schematic plan view and a schematic cross-sectional perspective view of an embodiment of a meniscal repair device according to the invention.

A three-dimensional fibre lay of silk fibres—both circumferential (8) and radial (not shown)—has been impregnated partially with a porous regenerated silk fibroin hydrogel and partially with a non-porous regenerated silk fibroin hydrogel to form the device.

The device of FIGS. 1 and 2 consists of a coronary ligament analogue (1) attached to a porous peripheral band (6) which is in turn attached to both a central, non-porous region (2) and a meniscofemoral ligament analogue (4). The attachment of the porous peripheral band (6) to the non-porous region occurs along a limit of the porous peripheral band (7). A central former (3) has been used to facilitate manufacture of the meniscal repair device. This central former (3) is excised prior to use along a line of cut (5).

Thus the anatomically-shaped meniscal repair device consists of a biomimetic fibre lay and a porous hydrogel lying between the fibres of the fibre lay. The fibre lay mimics that of the collagen fibres in the human meniscus. The orientation of the fibres of the fibrelay is therefore substantially circumferential with a smaller number of radially-orientated fibres stitched or woven through the circumferential fibres. The radial fibres also serve to keep spaces open between the circumferential fibres to accommodate the hydrogel.

The circumferential orientation of the fibres is continued into the meniscofemoral ligament analogue (4) (a marginal flange or extension of one or both of the horns of the crescent moon-shaped body of the device) to provide a means of anchoring the device to bone. The meniscofemoral ligament analogue (4) is mineralised with hydroxyapatite by dip coating or immersing in simulated body fluid.

The biomimetic fibre lay gives the meniscal repair device anisotropic mechanical properties similar to those of a natural knee meniscus.

The fibre lay of the meniscal repair device uses a combination of winding and stitching with the circumferential fibres (8) being laid down by winding and the radial fibres being stitched round and into the circumferential fibres to tie them together. The meniscal repair device can alternatively be produced by weaving, twisting, braiding, knitting, or embroidery or a combination of these.

The fibre lay can also be produced by stitching successive layers of fabric together. In this case the circumferential orientation of the fibres in the fibre lay is achieved by using a fabric with a higher density of warp fibres than weft fibres and folding the fabric on itself so that the warp fibres are approximately circumferential in orientation.

The fibre lay of the device is comprised of bioresorbable silk fibres—such as strong and tough polyalanine silk fibres whose fibroin contains at least eight repeats of the integrin-binding triplet RGD. Alternatively, these may be fibres of natural mulberry silk, of another natural wild silk or of natural spider silk. Alternatively, they may be fibres extruded from regenerated mulberry, wild or spider silk or fibres extruded from a recombinant protein based on the proteins of mulberry silk, wild silk or spider silk or a combination of these.

The silk fibre lay consists of strands of degummed or raw silk consisting of six to nine silk baves lightly twisted round each other. Alternatively, the silk fibre lay may be formed from silk sliver fibres, from silk thread formed by twisting silk sliver fibres, from silk monofilaments, from silk monofilaments twisted together, from undegummed silk baves, from degummed silk brins, from threads formed from two to eight former strands twisted together or from silk threads plaited or braided together.

The hydrogel has an open pore structure and consists of native or regenerated silk fibroin from mulberry, wild or spider silk. Alternatively the hydrogel may consist of gelatin, fibrin, fibronectin, alginate, hyaluronic acid, chondroitin sulphate or a combination of these.

Where the porous hydrogel is proteinaceous it can be cross-linked by immersion in a covalent cross-linking agent.

Where the porous hydrogel is comprised of fibroin it can be cross-linked by hydrogen bonds by treatment with 30-70% ethanol.

Either form of cross-linking influences the mechanical properties and resorption time of the both the hydrogel and the silk fibre lay. A range of different cross-linking agents may be used to cross-link hydrogels of different compositions. For example these include: members of the aliphatic aldehyde series, dialdehydes, carbodiimides, succinimides, succinamides, peroxidases in the presence of hydrogen peroxide, transglutaminases, phenoloxidases, phenolases, tyrosinases and/or Fenton reaction catalysts.

The resorption time can also be tuned by varying the hydrophobicity of the protein or proteins by alkylating with hydrophobic side chains. Hydrophilic carboxyl, hydroxyl, amine and sulphydryl side chains of amino acids within silk proteins may be used as sites for such acylation. Alternatively, a wide range of monofunctional, bifunctional or polyfunctional acylating agents may be used to increase the hydrophobicity of proteins. In the case of bi- or polyfunctional acylating agents these have the additional effect of cross-linking the protein components. Acylating agents that can be used to increase the hydrophobicity of the proteins include, for example, arylating and alkylating agents. Further acylating agents suitable for increasing the hydrophobicity of the proteins include perfluorobutanoyl chloride, lauroyl chloride, myristoyl chloride, benzophenonetetracarboxylic acid, diaminodiphenyloxide, aliphatic and bifunctional isocyanates, dodecyl ioscyanate, hexamethylene diisocyanate, aliphatic anhydrides and octadecenyl succinic anhydride.

One or more growth factors are incorporated in or covalently bound to the hydrogel of the body of the device (2, 6). These growth factors stimulate the binding and/or differentiation of mesenchymal or stem cells to either form cartilage or to secrete protoglycan. Suitable growth factors include Beta-FGF, TGF-beta 1, GDF-5, insulin-like growth factor, basic fibroblast growth factor, cartilage tissue growth factor or osteogenic protein-1. One or more synthetic drugs with analogous functionality to the growth factors may be used to replace or augment the functionality of the natural growth factors.

Similarly one or more covalently bound growth factors are incorporated into the marginal flanges or extensions of the device (1, 4). These growth factors stimulate the recruitment, binding and/or differentiation of mesenchymal or stem cells to secrete normal bone. Suitable growth factors include a bone morphogenetic protein, a TGF-beta, an epidermal growth factor, an insulin-like growth factor, growth/differentiation factor-10 or Run×2 (Cbfa1/AML3) transcription factor. One or more covalently bound synthetic drugs with analogous functionality to the growth factors may be used to replace or augment the natural growth factors.

Living cells may be incorporated directly into a solution of ungelled fibroin and alginate monomers made up in modified cell culture media. The resulting cell suspension is then incorporated into the device either before completing the laying down of the fibre lay or into preformed hydrogel scaffolds. After incorporation, the alginate monomers are caused to polymerise. Living cell suspensions may be mixed with alginate solutions made up in low calcium cell culture medium. Such a mixture may subsequently be gelled by the addition of a cell-compatible concentration of calcium.

Similarly, regenerated silk fibroin solutions remain a sol in neutral or slightly alkaline cell culture medium but slowly form a gel when slightly acidified with phosphate buffer. This enables living cells to be incorporated into porous fibroin hydrogels.

Figure 3:
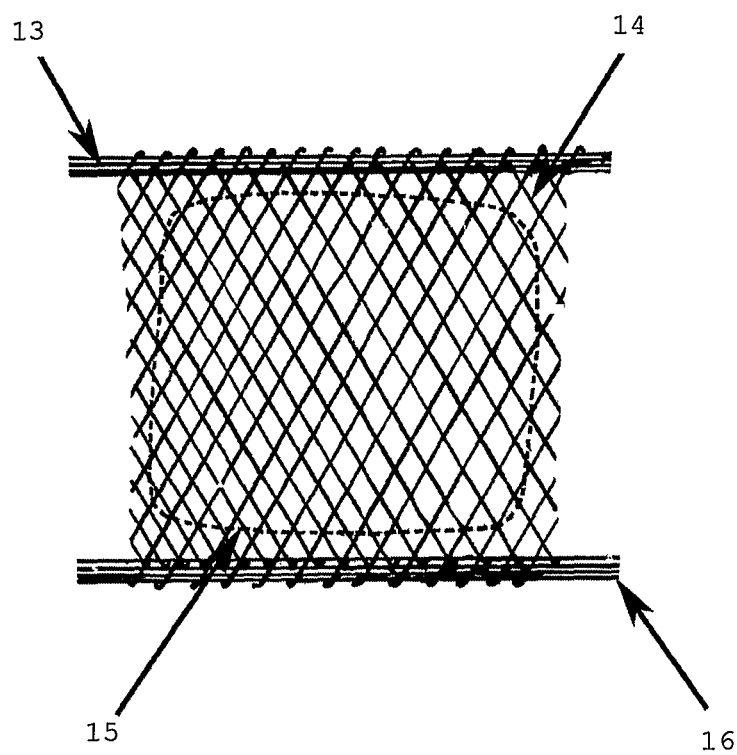
FIG. 3: A schematic drawing of an intervertebral disc repair device according to the invention.
Figure 4:
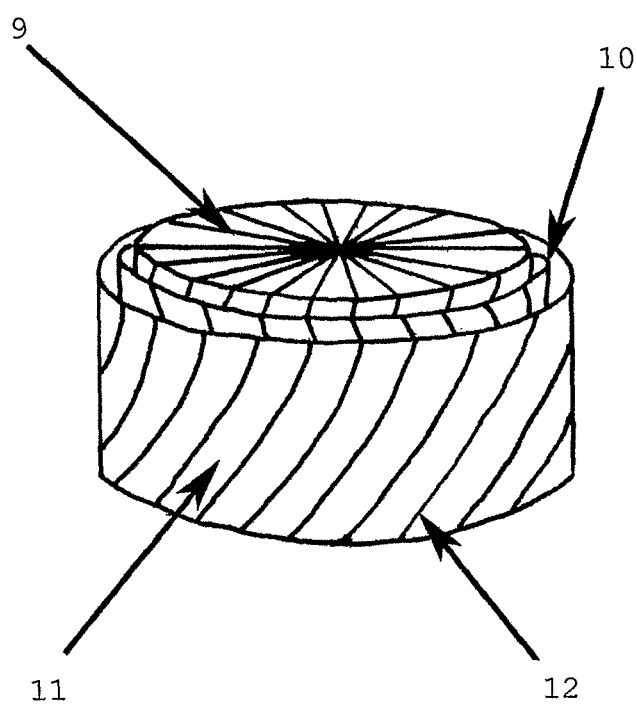
FIG. 4: A schematic perspective drawing of an intervertebral disc repair device according to the invention.

FIGS. 3 and 4 show a schematic representation of an embodiment of an intervertebral disc repair device according to the invention.

In this embodiment there is a cylindrical nucleus pulposa analogue (15) of regenerated silk fibroin hydrogel combined with randomly oriented silk fibres (not shown). This nucleus pulposa analogue (15) forms the core around which an annulus fibrosa analogue (14) is laid. The annulus fibrosa analogue (14) consists of silk fibres laid down around the nucleus pulposa analogue (15) in a trellis-like arrangement. Premineralised sheets of fibrelay and hydrogel (13, 16) are incorporated into the device as successive layers of the annulus fibrosa analogue (14) are laid down. The premineralised sheets (13, 16) form the top and bottom of the device and facilitate the integration of the device with the bony surface of the vertebral centrum of a patient. The premineralised sheets (13, 16) are extended laterally beyond the annulus fibrosa analogue (14) in order to facilitate anchoring of the device to the bony surfaces of the vertebral centra.

The three-dimensional fibre lay consists of layers of radially oriented silk fibres at the top and bottom of the device (9) together with silk fibres laid down in successive concentric cylindrical layers (10). A porous regenerated silk fibroin hydrogel (11) holds the fibres and layers of fibres together. The fibres in any particular cylindrical layer are laid down parallel to one another and are tilted at a constant angle to the vertical axis of the device (12). The tilt of the fibres alternates to left and right in successive cylindrical layers to form a trellis-like structure (12).

The anatomically-shaped intervertebral disc repair device closely resembles the meniscal repair device described above other than in the nature of the fibre lay.

The fibre lay of the intervertebral disc repair device also uses a combination of winding and stitching, though can alternatively be produced by weaving, twisting, braiding, knitting, or embroidery or a combination of these.

The fibre lay of the intervertebral repair device basically has three components: a nucleus pulposa analogue (15), an annulus fibrosa analogue (14) and top and bottom surfaces (13, 16) with flanges for attachment into the bone of the two adjacent vertebral centra.

The fibre lay of the nucleus pulposa analogue (15) is substantially cylindrical and comprises a loose meshwork of randomly orientated silk fibres infiltrated with a porous hydrogel matrix. The fibre lay of the annulus fibrosa analogue (14) consists of a succession of cylindrical lamellae closely investing the nucleus pulposa analogue (15). The fibres are arranged parallel to one another in each lamella and at a substantially constant angle to the vertical axis of the device. The fibres in successive lamellae are tilted alternately to right and left maintaining a substantially constant angle of tilt throughout the annulus fibrosa analogue (14) and giving it a trellis-like structure. A porous hydrogel fills the space between the lamellae and the space between the fibres within the lamellae.

An alternative fibre lay (not shown) for the annulus fibrosa (14) is formed from a bandage-like strip of silk cloth wound round the nucleus pulposa analogue (15) to give a concentric Swiss roll structure. The silk strip is first cut on the bias and stretched until the angle between the warp and weft fibres is twice the angle of tilt of the collagen fibres in the healthy intervertebral disc. The strip is heavily impregnated with a solution of the monomer used to form the hydrogel matrix and successive layers of this solution are applied as the strip is wound around. Isosceles triangles may be cut into the top and bottom edge of the strip to help form the top and bottom surface of the device.

The top and bottom surfaces (13, 16) of the intervertebral disc repair device and flanges for attachment to the bone consist of a plurality of layers of mineralised fibres and hydrogel. These layers may be stitched to the ends of the annulus fibrosus analogue (14) or constructed from the same cloth or windings used to form this component.

Figure 5:
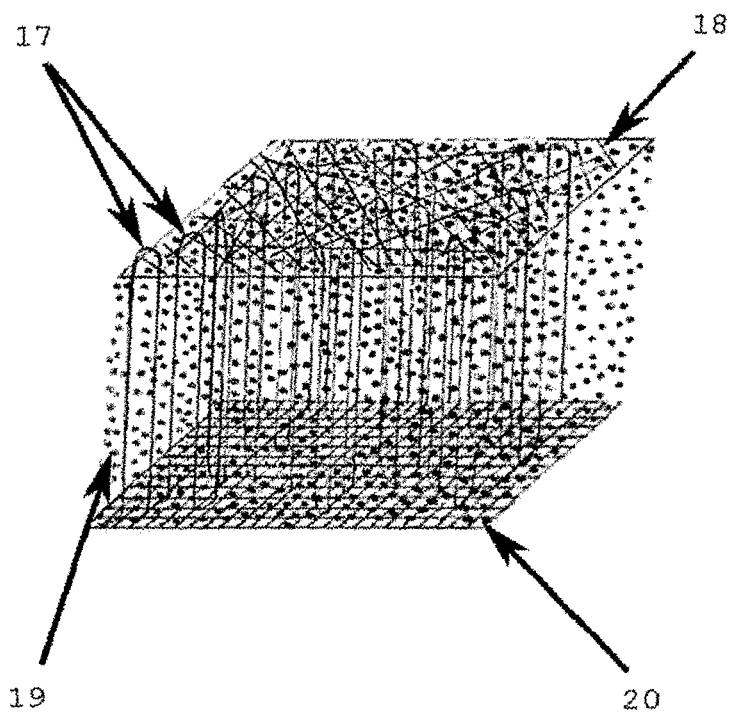
FIG. 5: A schematic perspective drawing of an articular cartilage repair device according to the invention.

FIG. 5 shows a schematic representation of an embodiment of an articular cartilage repair device according to the invention. In this embodiment, a base of the device (20) is formed of layers of mineralised silk fibre lay and regenerated silk fibroin hydrogel. These mineralised base layers (20) facilitate anchoring of the device to the subchondral bone. A layer of stiff hydrogel (19) is laid on top of the mineralised base layers (20). This stiff hydrogel layer (19) incorporates chondroblasts. An analogue of the arcade structure of articular cartilage is formed by looped fibres (17) which are stitched through the mineralised base layers (20) and run up through the stiff hydrogel layer (19) perpendicular to the base layers (20). The top and bottom of these fibre loops (17) are held in place by tie yarn (not shown). Top layers (18) consist of regenerated silk fibroin hydrogel impregnated into a tangentially oriented fibre lay—such as tie yarn or silk cloth. These top layers (18) provide a smooth articular surface for the device. Chondroblasts may also be incorporated into the top layers (18).

The biomimetic articular cartilage repair device closely resembles the meniscal repair device and the intervertebral disc repair device described above other than in the nature of the fibre lay.

The fibre lay of the articular cartilage repair device uses stitching though it can alternatively be produced by weaving, winding, twisting, braiding, knitting, or embroidery or a combination of these.

The fibre lay of the articular cartilage repair device basically has three components: a base layer (20) with marginal flanges for attachment to bone, a central layer (17, 19) and a superficial layer (18). The base layer (20) consists of a plurality of layers of mineralised cloth and porous hydrogel forming a surface for attachment to the bone. The central layer consists of stiff (hence non-flowable) porous hydrogel (19) through which silk fibre loops (17) are stitched in such a way as to mimic the arcade structure of healthy articular cartilage. The silk fibre loops may be produced by a sewing machine and held in place by a locking thread. The superficial layer (18) is formed from a plurality of sheets of silk cloth or lamellae of fibres through which the arcade fibres are stitched. The hydrogel in the uppermost lamellae of the superficial layer is non-porous to give a smooth and stiff articular surface. Chondroblasts or mesenchymal stem cells may be incorporated into the monomer of the hydrogel throughout the device before it is polymerised under physiological conditions, noting that fibroin and alginate solutions can be gelled under conditions which maintain cell viability. The former require slightly acidic conditions and the latter slightly elevated calcium levels for gelation.

Figure 6:
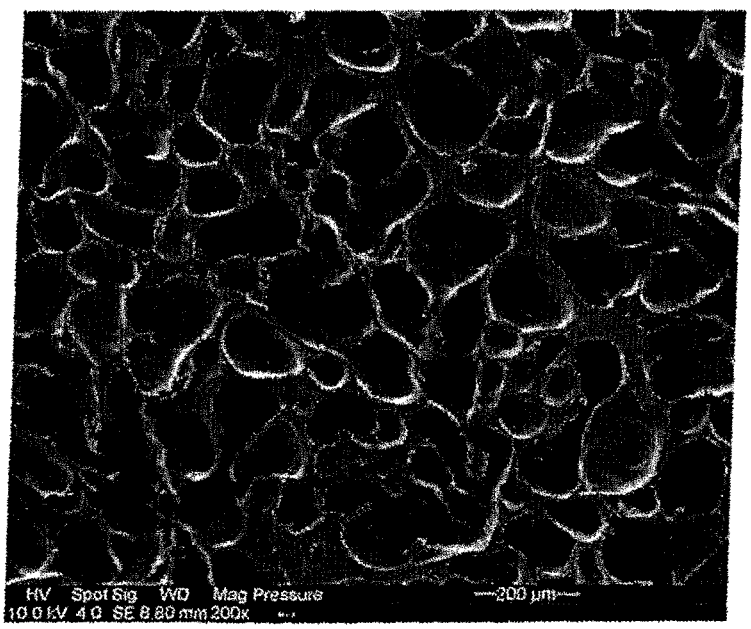
FIG. 6: Scanning electron micrograph (SEM) image showing the microporous structure of a porous hydrogel according to the invention.

FIG. 6 is a scanning electron micrograph of a hydrogel prepared from *Bombyx mori* regenerated silk fibroin according to protocol A below. The pores (23) of the hydrogel may be clearly seen in this image.

Figure 7:
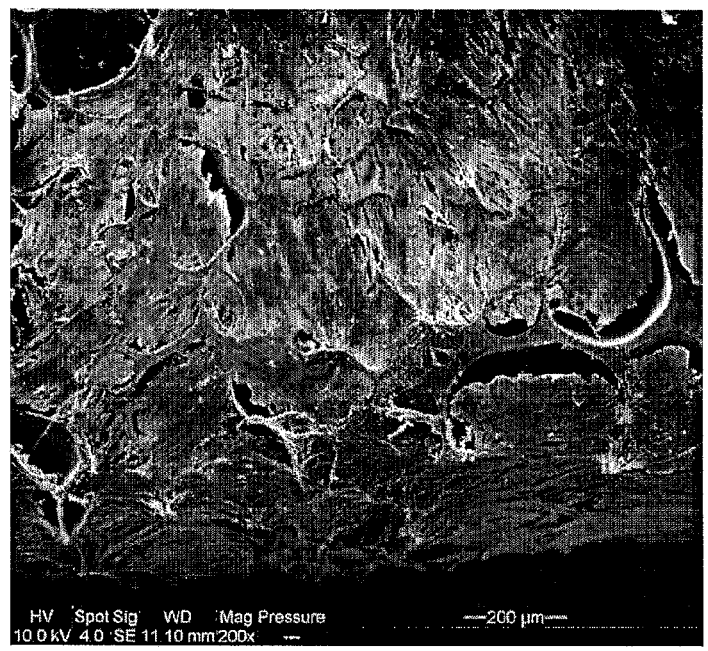
FIG. 7: The porous hydrogel of FIG. 6 after seeding with primary human bone marrow stromal cells.

FIG. 7 is a scanning electron micrograph of a porous gel as depicted in FIG. 6, but after seeding with human bone marrow stromal cells from clones selected for strom 1 activity and grown in basal alpha MEM medium with 10% fetal calf serum and 1% penstrep at 37 degrees C. in 5% CO2 for the first 7 days, then for 3 days in the same medium but made osteogenic by the inclusion of dexamethasone and ascorbic acid. Viable cells have completely filled the pores (23) at the surface of the device showing that the device has good adhesiveness to cells and excellent cytocompatibility. The cells have differentiated successfully into osteoblasts (as indicated in tests by reacting positively for alkaline phosphatase).

Figure 8:
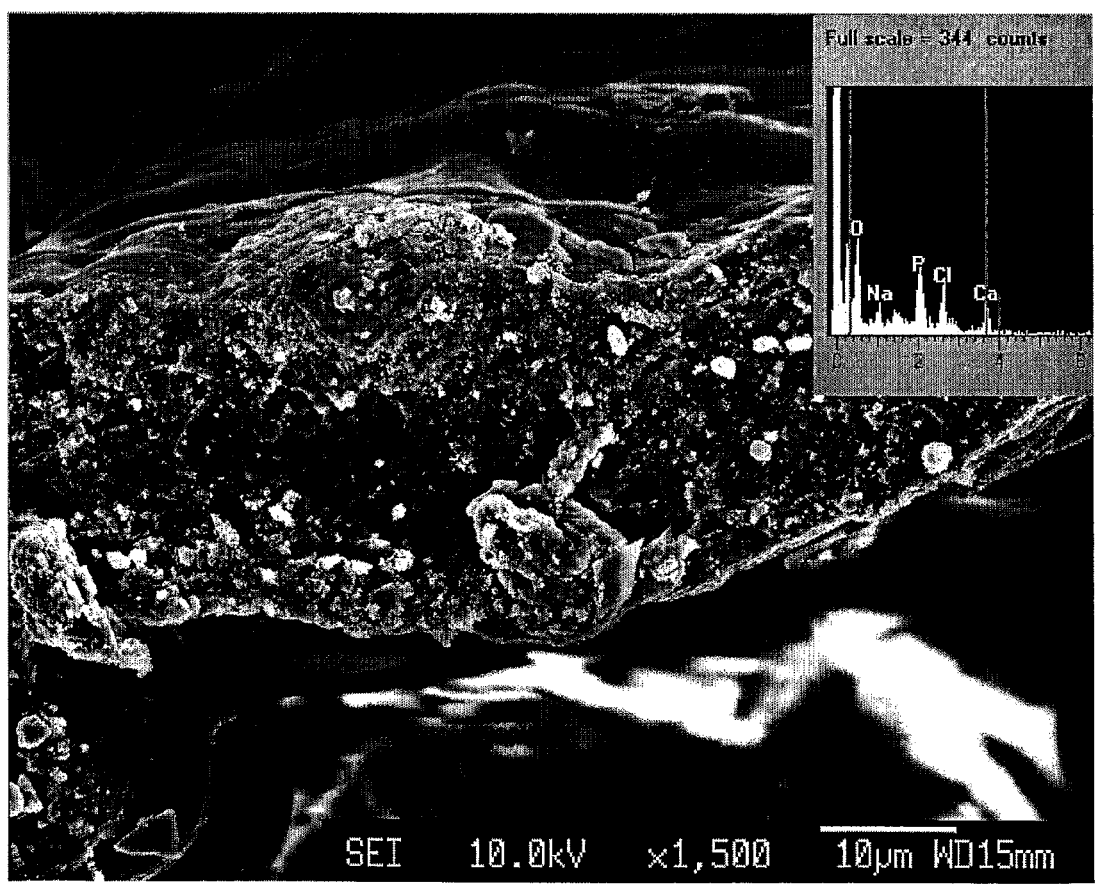
FIG. 8: Scanning electron micrograph (SEM) showing a transversely fractured pore wall of a mineralised hydrogel prepared according to the invention.
Figure 9:
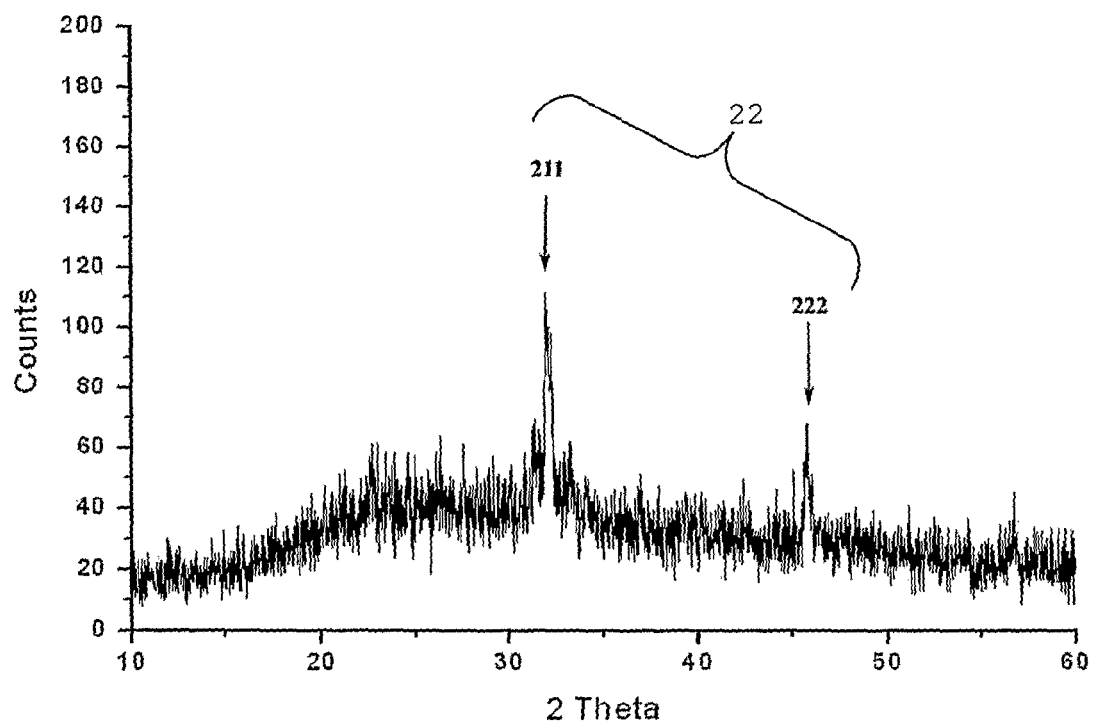
FIG. 9: X-ray diffraction plot from a mineralised fibroin hydrogel prepared according to the invention.
Figure 10:
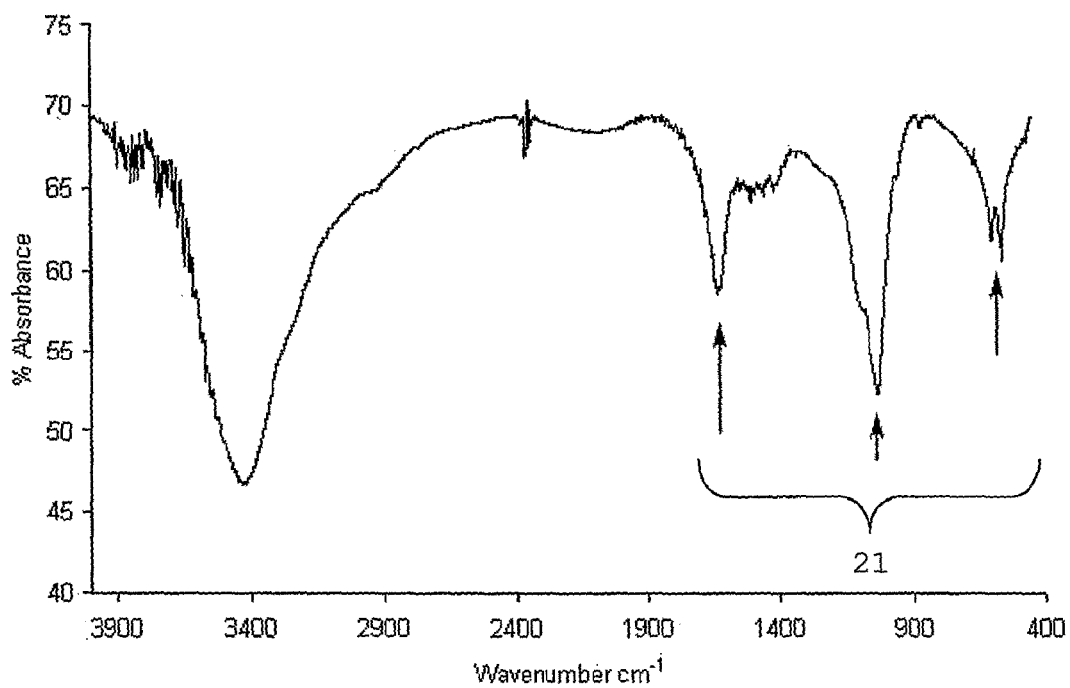
FIG. 10: Fourier transform infra red spectrum from a mineralised fibroin hydrogel prepared according to the invention.

FIG. 8 is a scanning electron micrograph together with (inset) an energy dispersive X-ray spectrum of a transversely fractured pore wall of a mineralised fibroin hydrogel, prepared according to protocol C below. The cut surface shows impregnated hydroxyapetite (as indicated by the plate-like crystals and also by the X-ray diffraction plot (FIG. 9) from a mineralised fibroin hydrogel prepared according to protocol C below in which the arrowed peaks (22) show the 211 and 222 reflections characteristic of hydroxyapetite). The presence of a calcium phosphate mineral such as hydroxyapetite is also indicated in the energy dispersive X-ray spectrum by the prominent peaks for calcium, phosphorous and oxygen and in the Fourier transform infra-red spectrum (FIG. 10) of a mineralised fibroin hydrogel prepared according to protocol C below; the arrowed peaks (21) of which demonstrate the presence of calcium phosphate.

PROTOCOL A: Preparation of Porous Gels from Native Fibroin.

1. Prepare a circa 20 w/v % solution of degummed *Bombyx mori* silk by dissolving 20 g/100 ml 9.3M LiBr solution at 60 degrees C. for 4 hours with continuous stirring. Transfer to a weighed dialysis tube (preferably MWCO 3500 or smaller). Dialyse against 5 changes of deionised water for 2 days at 4 degrees C. The resulting solution should be about 8% w/v. Partially dry within the dialysis bag in a vacuum desiccator until the desired protein concentration (between 8-15% w/v) has been reached as assessed by refractometry or by gravimetry after drying samples to constant weight in a vacuum oven heated to 50 degrees C. Gently squeeze contents of dialysis tube down and reclip bag so that the protein solution completely fills the clipped off length of tubing.
2. Dialyse samples against 0.5-1% acetic acid for not longer than 12 hours at 4 degrees C.
3. Alternatively treat small drops of concentrated fibroin solution with vapour from 0.1% acetic acid or add 10 μl of 1 M sodium citrate buffer (pH 5.0) to 1 ml of concentrated fibroin and immediately transfer to a cylindrical mould before leaving for 12 hours to gel.
4. Freeze at −50 degrees C. for 20 minutes.
5. The material is sufficiently stiff (compressive modulus about 1 MPa at optimal protein concentrations) to give good hand sections which can be mounted in water and observed by polarizing or differential interference microscopy to determine pore size distribution and density of interconnecting pores. Material should also be subjected to critical point drying and examined with a SEM.
6. The intercommunication of pores may be rapidly assessed by squeezing of the wet gel between thumb and forefinger. A high level of intercommunication of the pores is indicated by rapid outflow of water followed by an inflow of air into all parts of the gel on relaxing pressure.

PROTOCOL B: Preparation of Meniscal Repair Device.

1. A cylindrical Lucite former with a diameter equal to that of the internal diameter of the crescent-shaped meniscal repair device is to be used. A sausage-shaped core of approximately randomly orientated wild silk fibres is infiltrated with fresh 8-12% w/v silk fibroin solution prepared as described in Protocol A. The fibroin is gelled by immersion of the core in dilute sodium citrate buffer at pH 4.5. Pieces of degummed wild silk cloth with a loose weave are cut to an appropriate approximately kidney shape and coated with fibroin solution. Layers are added successively to build up the crescent shape of the device. Each layer is stitched to the one beneath with braided wild silk suture with throws to mimic the circumferential fibres of the device. Some radial stitches are also made. The radial width of the silk pieces is reduced to produce the wedge shaped profile of the device. A peripheral flange and medial ligament analogue is also included and stitched at appropriate stages while building up the body of the device.
2. The windings on the opposite side of the former to the body of the device are cut and the whole structure removed from the former.
3. The fibroin matrix is gelled as described in protocol C below by immersing the whole device in 0.1-1.5 M sodium phosphate solution buffered to pH 6.3 at 4 degrees C. for between 4-16 hours. Alternatively fibroin matrix within the device can be gelled by immersion in 0.1-1% acetic acid for 12 hours or by exposure to vapour from 0.1% w/v acetic acid—in both instances for 12 hours at 4 degrees C.
4. The matrix was frozen rapidly at −50 degrees C. to generate a porous architecture.
5. The structure is hardened by transferring it to 50% ethanol and stored in this solution or cross-linked in 10-25% glutaraldehyde, exhaustively washed and reduced in aqueous 0.1% sodium borohydride until no more hydrogen is evolved.
6. The resulting composite is remarkably stiff and strong and has an open porous architecture.

PROTOCOL C: Production of Mineralised Silk Proteins
1. 0.1-1.5M phosphate solutions are prepared using sodium dihydrogen phosphate. 1 g of 0.08M Trizma base is added per 100 ml of phosphate solution and the pH is adjusted with drops of 10 to 1M HCl to give a range of pH values between 6.3-9.0.
2. Dialysis bags containing 10% w/v fibroin solution are prepared as in protocol A. The bags are then placed in one of the Tris buffered phosphate solutions prepared in step 1 and kept at 4 degrees C. for between 4-16 hours to gel the silk protein and introduce phosphate ions.
3. The dialysis bags containing the fibroin are rapidly frozen at −20 degrees C. to introduce a porous structure and then thawed at room temperature. The freeze-thaw cycle may be repeated up to 5 times to increase the interconnectivity of the pores.
4. Thawed gels are removed from the dialysis tubing and, for most applications, the impermeable surface layer of the gels is removed using a sharp scalpel. The silk gels are then cut into cubes for further treatments.
5. The cubes of gel are freeze-dried and then transferred to 0.25-2.5M calcium chloride solutions buffered to pH 7.0-9.0 with Tris HCl as in step 1. The pieces of gel are left for 24 hours at 37 degrees C. in this solution. Alternatively, the cubes of gel may be transferred directly to a buffered calcium chloride solution without freeze drying or may be air dried at 20 degrees C. before transfer to the buffered calcium chloride solution.
6. Silk fibre lays incorporating gelled fibroin prepared as described in protocol B can be mineralized using the same procedure with or without enclosing them in dialysis membrane.

There are several methods for preparing concentrated solutions of regenerated silk fibroin by dissolving degummed cocoons, fibroin powder or degummed silk fibres in a chaotropic agent.

Also several different methods may be used to introduce hydrogel into the interstices of the fibre lay. These include spraying, dipping, painting, injecting or vacuum infiltration.

Hydrogel may be applied at several stages during the creation of a fibre lay to obtain better penetration of matrix into the fibre lay than can be obtained by applying the hydrogel after completion of the fibre lay.

Also, hydrogel may be applied in a partially dehydrated or deswelled state and subsequently fully swollen in tissue fluid in order to provide turgor pressure to help stiffen the implantable material.

The fibres or fabric used to form the fibre lay may be coated with hydrogel before the fibre lay is formed.

The porous hydrogel may be concentrated in the fibre lay to a desired protein concentration by allowing some of the water to evaporate. If an initial fibroin concentration and wet weight are known, the fibroin can be brought to a desired final concentration by allowing some of the water to evaporate until a defined weight loss is produced. A 10-12% final protein concentration gives good results. Once the desired protein concentration has been reached, the fibroin sol is then gelled.

A number of methods can be used for inducing gelation of a fibroin sol. For example, these include immersion in acidic buffers at a pH between 3.5 and 6.4, treatment with vapour from a mildly acidic volatile buffer such as ammonium acetate or immersion/vapour treatment with aqueous alcoholic solutions.

A porous structure with a high density of intercommunicating pores with fairly uniform diameter distribution can be readily be produced by rapid freezing. Intercommunicating pores with mean pore sizes from 50-300 μm may be produced by varying protein concentration and length of exposure to acid.

An anisotropic porous structure may be produced by controlling the direction of movement of a freezing zone across the material.

Even without a fibre lay, the porous hydrogel formed by acid gelation of fibroin followed by freezing has a compressive stiffness of between 1-2 MPa—in the range of articular cartilage (1-20 MPa).

Other methods can be used for rendering the hydrogel matrix porous. These include, for example, thermally induced phase separation, solvent casting and particle leaching, supercirtical gas foaming, salt leaching with particulate sodium chloride, freeze drying, mixing the fibroin with a water-miscible polymer capable of inducing the microphase separation, partially dissolving silk fibres with formic acid and sticking them together in a porous felt, incorporating additional soluble fibres into the silk fibres of the fibre lay that can be extracted after polymerising the hydrogel and applying insufficient protein to the fibre lay to completely fill the interstices.

A pore size of 70-120 μm is to be preferred for the porous hydrogel. This value is a compromise between the optimum value to allow for cell infiltration (approximately 150-300 μm) and the need for a low pore density to optimize the compressive properties of the hydrogel.

Once the porous hydrogel has been prepared it may be advantageous to add a cross-linking agent to stabilize it and bind it firmly to the silk fiber lay.

A range of cross-linking agents may be used to cross-link hydrogels of different compositions. For example, these include members of the aliphatic aldehyde series, dialdehydes, carbodiimides, succinimides, succinamides, peroxidases in the presence of hydrogen peroxide, transglutaminases, phenoloxidases, phenolases, tyrosinases, ruthenium (II) tris-bipyridyl in the presence of ammonium persulfate followed by light treatment, Fenton reaction catalysts, 10-60% w/v methanol or ethanol and 10-40% formic acid.

In the case of alginates, stable hydrogels may be prepared by the addition of moderate concentrations of calcium ions.

More than one cross-linking agent applied consecutively or together. Alternatively or additionally, the implantable devices may be cross-linked and/or sterilized by gamma irradiation, neutron irradiation, or high voltage discharge.

Porous fibroin hydrogel may be treated with 50% ethanol for 1 hour at room temperature to increase the formation of intermolecular beta sheet hydrogen bonds.

Porous hydrogel may also be treated with 10-50% glutaraldehyde to covalently cross-link the porous gel.

After exhaustive washing in water the hydrogel may be treated with freshly prepared aqueous 0.1% sodium borohydride at 4 degrees C. until no more hydrogen is evolved. This stabilizes the resulting aldimine cross-links formed by reaction with the arginine and lysine groups of fibroin. It also reduces any remaining unreacted aldehyde groups to non-toxic alcoholic ones. These two mechanisms greatly reduce the toxicity produced by glutaraldehyde cross-linking.

Aqueous formic acid solutions have two effects on dry silk fibroin: making it sticky by swelling or partially dissolving it and cross-linking it by inducing the formation of intra- and inter-molecular β-sheet hydrogen bonds. Due to this, a porous cross-linked fibre lay may be prepared by adding formic acid to a silk fibre lay which is then allowed to dry. Using this method, pore size may then be varied by stretching, compressing or bending the fibre lay. Powdered fibroin may be introduced to partially or substantially fill the interstices of the fibre lay before treatment with formic acid.

Cross-linking both the fibre lay and hydrogel components of the implantable device has the additional advantage of increasing the resorption time of these components of a device. Thus the extent of covalent cross-linking can be used as a method of tuning the resorption rates of these components. Addition of an acylating agent capable of substituting a hydrophobic group into a hydrophilic side chain provides an additional method of tuning the resorption rate of both fibre lay and hydrogel. Hydrophilic carboxyl, hydroxyl, amine and sulphydryl side chains of amino acids within silk proteins may be used as sites for acylation. A wide range of monofunctional, bifunctional or polyfunctional acylating agents may be used to increase the hydrophobicity of proteins. In the case of bi- or polyfunctional acylating agents these have the additional effect of cross-linking the protein components. Acylating agents that can be used to increase the hydrophobicity of the proteins include, for example, acylating and alkylating agents. Acylating agents suitable for increasing the hydrophobicity of proteins include, for example, perfluorobutanoyl chloride, lauroyl chloride, myristoyl chloride, benzophenonetetracarboxylic acid, diaminodiphenyloxide, aliphatic and bifunctional isocyanates, dodecyl ioscyanate, hexamethylene diisocyanate, aliphatic anhydrides, octadecenyl succinic anhydride.

The relatively high compressive modulus of the device and hence its resistance to compression is dependent in part on the swelling pressure of the hydrogel constrained within the fibre lay. This is because the swelling of the hydrogel pre-stresses the fibre lay so that even a slight bending or compression of the device results in an immediate marked increase in stress of the fibres. The stiffness and strength of the composite material arises in part because an application of a bending or compressive force increases the hydrostatic pressure in the hydrogel matrix and this force per unit area is immediately transferred to the pre-stressed fibres. It is accordingly desirable that the hydrogel within the fibre lay is treated with a cross-linking agent in a state in which it is incompletely swollen and in such a way that it will tend to hydrate further and swell after cross-linking or when implanted into the patient. This can be achieved, for example, using one or a combination of the following methods: partially removing the water from the hydrogel before and during cross-linking by adding a colloid such as polyvinylpyrolidone or polyethyleneglycol to sequester some of the water, partially removing some or all of the water before and during cross-linking freeze drying, using an organic co-solvent or a solvent system containing a substantially reduced concentration of water for the drying and cross-linking, subjecting the fibre lay and constrained hydrogel to hydrostatic pressure or compressive loading before and during the cross-linking reaction and adding or removing salts and/or controlling the pH to reduce the swelling of the hydrogel before and during cross-linking.

Also, the fibre lay may be pre-stressed by winding almost all of it in a taught state while applying layers of partially hydrated hydrogel as described above before cross-linking using a chemical agent or irradiation or electrical discharge or photopolymerisation.

A taughtly wound fibre lay containing, in a substantially dehydrated state, either the hydrogel or monomers for forming the hydrogel may be cross-linked with a concentrated solution of glutaraldehyde and/or formaldehyde also comprising polyvinylpyrolidone or polyethyleneglycol.

A hydrogel may be given different properties in different parts of the device by applying the component or components for forming the hydrogel in successive layers or regions receiving different treatments.

In addition to forming a hydrogel within the fibre lay, the component or components for forming the hydrogel may be applied to form a coating to the fibre lay.

The open porosity of all or part of the device allows for infiltration in vitro or in vivo of living stem cells into the pores of the device. A patient's own living stem cells or those from a donor may be allowed to enter the pores of the device before implantation. Implants infiltrated with stem cells may be immediately implanted or kept in vitro under conditions known to enhance the formation of hyaline or fibrocartilage. In either case, this provides the implant with cells for subsequent formation of living cartilage. Alternatively a patient's own mesenchymal stem cells may be introduced into the porous hydrogel after implantation. However incorporation of cells before implantation may enhance the rate of synthesis of new functional tissues, and in particular, the rate at which a fully functional anchorage of the device into bone is produced.

Both the porous hydrogel and the fibre component of the fibre lay of the one or more extensions or surfaces may be mineralised with the bone mineral hydroxyapatite thereby producing a material that substantially mimics bone in its physical properties, is osteoconductive and osteoinductive, is biocompatible and serves as an attachment site for mesenchymal cells and in these ways facilitates the attachment and integration of the device to the underlying bone.

The silk fibroin solution in the hydrogel may first be gelled with a weakly acidic solution containing phosphate ions and, after freezing to create a porous matrix, the material may be treated with a solution containing calcium ions to form hydroxyapatite. Alternatively hydroxyapatite may be deposited in the fibre lay and porous hydrogel after cross-linking by repeated alternating dippings for 1 hour in 120 mM disodium hydrogen phosphate at pH 7. followed by 1 hour in 200 mM calcium chloride solution at pH 7.4 all at 20 degrees C. A further alternative is to treat fibre lay and enclosed hydrogel with simulated body fluid. In this case citric acid may be added to act as a nucleating agent at the surface.

One or more extensions to the device may be mineralised by the extension being immersed in the mineralising solutions described in protocol C without mineralising the remainder of the device. Where it is desired to mineralise one or more surfaces or outer layers of the device the surface may be immersed or otherwise treated with a thin layer of the mineralizing solutions.

A thin waterproof biocompatible membrane may be incorporated into the device during the preparation of the fibre lay to limit the spread of mineralising solutions to the desired surface or surfaces.

A layer or layers or extensions may be prepared separately and subsequently mineralized before being stitched or otherwise attached to non-mineralised component or components of the device. The mineralised hydrogel may be used on its own as a material for the repair of bone or the fixation of orthopaedic devices (e.g. endoprostheses) in bone.

The device is intended for the repair of defects in articular cartilage or the partial or complete replacement of one or both menisci of the knee or the temporomandibular meniscus or the replacement of one or more intervertebral discs.

The invention claimed is:

1. An implantable cartilaginous tissue repair device comprising:
    a biocompatible and at least partially bioresorbable three-dimensional fibre lay comprising silk fibres
    at least partially infiltrated by
    a biocompatible and at least partially bioresorbable, substantially porous hydrogel comprising silk protein cross-linked by hydrogen bonds to form a beta sheet configuration, the hydrogel being cross-linked to the fibre lay,
    wherein the hydrogel is non-flowable and has an open pore structure,
    whereby, in use, cells can be introduced into and contained within at least some pores of the open pore structure of the hydrogel.

2. An implantable cartilaginous tissue repair device according to claim 1 in which said three-dimensional fibre lay is substantially biomimetic of the fibre pattern of a cartilaginous tissue which is to be repaired.

3. An implantable cartilaginous tissue repair device according to claim 1 in which the three-dimensional fibre lay comprises fibres selected from the group consisting of: natural mulberry-silk fibres, natural wild-silk fibres, spider-silk fibres, fibres of a recombinant protein based substantially on the proteins of mulberry silk, fibres of a recombinant protein based substantially on the proteins of wild silk, and fibres of a recombinant protein based substantially on the proteins of spider silk.

4. An implantable cartilaginous tissue repair device according to claim 1 in which said substantially porous hydrogel comprises at least one component selected from the group consisting of: regenerated silk fibroin from mulberry silk and regenerated silk fibroin from wild silk.

5. An implantable cartilaginous tissue repair device according to claim 1 in which the average pore diameter is between 50 µm and 300 µm.

6. An implantable cartilaginous tissue repair device according to claim 1 further comprises:
    one or more covalently bound growth factors selected from the group consisting of: beta-fibroflast growth factor, transforming growth factor-beta 1, growth differentiation factor-5, insulin-like growth factor, basic fibroblast growth factor, cartilage tissue growth factor and osteogenic protein-I,
    whereby, the binding and/or differentiation of mesenchymal or stem cells is stimulated in order to either form cartilage or to stimulate protoglycan secretion.

7. An implantable cartilaginous tissue repair device according to claim 1 further comprises:
    an integral attachment means for attaching said three-dimensional fibre lay and said porous hydrogel to bone.

8. An implantable cartilaginous tissue repair device according to claim 7 in which said integral attachment means comprises at least one mineralised surface layer, extension or flange.

9. An implantable cartilaginous tissue repair device according to claim 8 in which said at least one mineralised surface layer, extension or flange comprises hydroxyapatite.

10. An implantable cartilaginous tissue repair device according to claim 7 in which said integral attachment means further comprises:
    one or more covalently bound growth factors selected from the group consisting of: a bone morphogenetic protein, a transforming growth factor-beta, an epidermal growth factor, an insulin-like growth factor, growth/differentiation factor-10 and Runx2 (Cbfa1/AML3) transcription factor
    whereby, the recruitment, binding and/or differentiation of mesenchymal or stem cells is stimulated in order to secrete normal bone.

11. An implantable cartilaginous tissue repair device according to claim 1 for total or partial replacement or augmentation of articular cartilage in which the orientation of the fibres in said three-dimensional fibre lay is substantially similar to the fibre orientation in a section of articular cartilage which is to be repaired.

12. An implantable cartilaginous tissue repair device according to claim 1 in which said three-dimensional fibre lay is formed as an arching arcade structure comprising:
    at least one substantially flat base layer;
    at least one substantially flat top articular surface layer which is substantially parallel to said base layer; and
    a plurality of looped fibres which:
    are stitched through said base layer;
    run substantially perpendicular to said base layer and to said top articular surface layer; and
    are held in place at the base layer and/or at the top articular surface layer by tying.

13. An implantable cartilaginous tissue repair device according to claim 1 in which the orientation of the fibres in said three-dimensional fibre lay is substantially similar to fibre orientation in an anatomical temporomandibular meniscus.

14. An implantable cartilaginous tissue repair device according to claim 1 in which said substantially porous hydrogel has an interconnecting pore structure.

15. An implantable cartilaginous tissue repair device according to claim 1 wherein the hydrogel is stiff.

16. An implantable cartilaginous tissue repair device according to claim 1 wherein not all of the pores contain cells.

17. An implantable tissue repair device comprising:
    a biocompatible and at least partially bioresorbable fibre lay comprising silk fibres at least partially infiltrated by:
    a biocompatible and at least partially bioresorbable porous hydrogel comprising silk protein cross-linked by hydrogen bonds to form a beta sheet configuration, the hydrogel being cross-linked to the fibre lay, wherein the hydrogel is non-flowable and has an open pore structure, whereby in use cells can be introduced into and contained within at least some pores of the open pore structure of the hydrogel, and
    an integral attachment means for attaching said fibre lay and said porous hydrogel to bone comprising at least one mineralised surface.

18. A method for total or partial replacement or augmentation of an intervertebral disc, the method comprising implanting an implantable cartilaginous tissue repair device according to claim 1 as a total or partial replacement or augmentation of an intervertebral disc, which device is substantially shaped like an anatomical intervertebral disc.

19. A method for total or partial replacement or augmentation of a knee meniscus, the method comprising implanting an implantable cartilaginous tissue repair device according to claim 1 for total or partial replacement or augmentation of a knee meniscus, which device is substantially shaped like an anatomical knee meniscus.

20. A method according to claim 19 in which said three-dimensional fibre lay comprises a plurality of fibres arranged substantially circumferentially and a plurality of fibres arranged substantially radially.

\* \* \* \* \*